(12) United States Patent
Smith et al.

(10) Patent No.: US 10,856,577 B2
(45) Date of Patent: Dec. 8, 2020

(54) PRODUCT USE AND BEHAVIOR MONITORING INSTRUMENT

(71) Applicant: RAI STRATEGIC HOLDINGS, INC., Winston-Salem, NC (US)

(72) Inventors: Jeffrey Sean Smith, Winston-Salem, NC (US); Steven L. Alderman, Lewisville, NC (US); Sarah A. Baxter-Wright, Winston-Salem, NC (US); John Darnell, Winston-Salem, NC (US); Kyung Soo (Jason) Hong, Winston-Salem, NC (US); Paul R. Nelson, Winston-Salem, NC (US); Elaine K. Round, Winston-Salem, NC (US); Stephen B. Sears, Siler City, NC (US); Rajesh Sur, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 49 days.

(21) Appl. No.: 15/710,681

(22) Filed: Sep. 20, 2017

(65) Prior Publication Data

US 2019/0082737 A1 Mar. 21, 2019

(51) Int. Cl.
*A24F 47/00* (2020.01)
*A61M 15/06* (2006.01)
(Continued)

(52) U.S. Cl.
CPC ........... *A24F 47/008* (2013.01); *A61M 15/06* (2013.01); *G16H 40/63* (2018.01); *G16H 40/67* (2018.01);
(Continued)

(58) Field of Classification Search
None
See application file for complete search history.

(56) References Cited

U.S. PATENT DOCUMENTS 2,974,669 A 3/1961 Ellis
4,714,082 A 12/1987 Banerjee et al.
(Continued)

FOREIGN PATENT DOCUMENTS

CN 104783331 A 7/2015
FR 2879746 A1 6/2006
(Continued)

OTHER PUBLICATIONS

International Search Report and Written Opinion from corresponding PCT Application No. PCT/US2018/051543, dated Dec. 20, 2018, pp. 1-22.
(Continued)

*Primary Examiner* — Michael H. Wilson
*Assistant Examiner* — Katherine A Will
(74) *Attorney, Agent, or Firm* — Foley & Lardner LLP

(57) ABSTRACT

A product use and behavior instrument includes a housing defining a central compartment therein. A controller is positioned within the central compartment. The controller includes a first connector. The first connector is configured to operatively and removably couple the product use and behavior instrument to a battery element. A second connector is configured to operatively and removably couple the product use and behavior instrument to a tank element. A sensor circuit is structured to collect at least one use data characteristic of a smoking action. The smoking action is associated with use of at least one of the tank and battery element. Local memory is structured to store the at least one use data characteristic of the smoking action. A communication interface is structured to communicate the stored at least one use data characteristic of the smoking action to a remote computing device.

28 Claims, 5 Drawing Sheets

(51) Int. Cl.
*G16H 40/67* (2018.01)
*G16H 40/63* (2018.01)
*A61M 11/04* (2006.01)
*A61M 16/00* (2006.01)
*G01N 19/00* (2006.01)
*G01N 27/00* (2006.01)
*A61M 15/00* (2006.01)

(52) U.S. Cl.
CPC ......... *A61M 11/042* (2014.02); *A61M 15/008* (2014.02); *A61M 2016/0015* (2013.01); *A61M 2016/0021* (2013.01); *A61M 2205/332* (2013.01); *A61M 2205/3331* (2013.01); *A61M 2205/3368* (2013.01); *A61M 2205/3375* (2013.01); *A61M 2205/3553* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2205/60* (2013.01); *A61M 2205/609* (2013.01); *A61M 2205/8206* (2013.01); *A61M 2209/00* (2013.01); *G01N 19/00* (2013.01); *G01N 27/00* (2013.01)

(56) References Cited

U.S. PATENT DOCUMENTS

| | | |
|---|---|---|
| 4,756,318 A | 7/1988 | Clearman et al. |
| 4,771,795 A | 9/1988 | White et al. |
| 4,793,365 A | 12/1988 | Sensabaugh et al. |
| 4,917,128 A | 4/1990 | Clearman et al. |
| 4,961,438 A | 10/1990 | Korte |
| 4,966,171 A | 10/1990 | Serrano et al. |
| 4,969,476 A | 11/1990 | Bale et al. |
| 4,991,606 A | 2/1991 | Serrano et al. |
| 5,020,548 A | 6/1991 | Farrier et al. |
| 5,033,483 A | 7/1991 | Clearman et al. |
| 5,040,551 A | 8/1991 | Schlatter et al. |
| 5,050,621 A | 9/1991 | Creighton et al. |
| 5,060,671 A | 10/1991 | Counts et al. |
| 5,065,776 A | 11/1991 | Lawson et al. |
| 5,076,296 A | 12/1991 | Nystrom et al. |
| 5,076,297 A | 12/1991 | Farrier et al. |
| 5,099,861 A | 3/1992 | Clearman et al. |
| 5,105,835 A | 4/1992 | Drewett et al. |
| 5,105,837 A | 4/1992 | Barnes et al. |
| 5,115,820 A | 5/1992 | Hauser et al. |
| 5,148,821 A | 9/1992 | Best et al. |
| 5,159,940 A | 11/1992 | Hayward et al. |
| 5,178,167 A | 1/1993 | Riggs et al. |
| 5,183,062 A | 2/1993 | Clearman et al. |
| 5,211,684 A | 5/1993 | Shannon et al. |
| 5,240,014 A | 8/1993 | Deevi et al. |
| 5,240,016 A | 8/1993 | Nichols et al. |
| 5,345,955 A | 9/1994 | Clearman et al. |
| 5,388,594 A | 2/1995 | Counts et al. |
| 5,551,451 A | 9/1996 | Riggs et al. |
| 5,595,577 A | 1/1997 | Bensalem et al. |
| 5,726,421 A | 3/1998 | Fleischhauer et al. |
| 5,819,751 A | 10/1998 | Barnes et al. |
| 6,089,857 A | 7/2000 | Matsuura et al. |
| 6,095,152 A | 8/2000 | Beven et al. |
| 6,578,584 B1 | 6/2003 | Beven et al. |
| 6,730,832 B1 | 5/2004 | Dominguez |
| 7,290,549 B2 | 11/2007 | Banerjee et al. |
| 7,481,226 B2 | 1/2009 | Cholet |
| 8,079,371 B2 | 12/2011 | Robinson et al. |
| 8,402,976 B2 | 3/2013 | Fernando et al. |
| 8,424,538 B2 | 4/2013 | Thomas et al. |
| 8,464,726 B2 | 6/2013 | Sebastian et al. |
| 8,469,035 B2 | 6/2013 | Banerjee et al. |
| 8,617,263 B2 | 12/2013 | Banerjee et al. |
| 8,851,081 B2 | 10/2014 | Fernando et al. |
| 9,016,274 B1 | 4/2015 | White |
| 9,078,474 B2 | 7/2015 | Thompson |
| 9,149,072 B2 | 10/2015 | Conner et al. |
| 9,214,268 B2 | 12/2015 | Difonzo et al. |
| 9,220,301 B2 | 12/2015 | Banerjee et al. |
| 9,301,546 B2 | 4/2016 | Thomas et al. |
| 9,332,784 B2 | 5/2016 | Banerjee et al. |
| 9,345,268 B2 | 5/2016 | Stone et al. |
| 9,439,453 B2 | 9/2016 | Conner et al. |
| 9,486,013 B2 | 11/2016 | Sebastian et al. |
| 9,788,571 B2 | 10/2017 | Conner et al. |
| 9,814,268 B2 | 11/2017 | Robinson et al. |
| 9,839,241 B2 | 12/2017 | Davidson et al. |
| 9,933,790 B2 | 4/2018 | Blackley |
| 2004/0031497 A1 | 2/2004 | Likness et al. |
| 2004/0177674 A1 | 9/2004 | Read et al. |
| 2011/0265806 A1 | 11/2011 | Alarcon et al. |
| 2013/0220315 A1 | 8/2013 | Conley et al. |
| 2013/0255702 A1 | 10/2013 | Griffith et al. |
| 2013/0255703 A1 | 10/2013 | Banerjee et al. |
| 2013/0284192 A1 | 10/2013 | Peleg et al. |
| 2014/0000638 A1 | 1/2014 | Sebastian et al. |
| 2014/0060554 A1 | 3/2014 | Collett et al. |
| 2014/0096781 A1 | 4/2014 | Sears et al. |
| 2014/0096782 A1 | 4/2014 | Ampolini et al. |
| 2015/0059780 A1 | 3/2015 | Davis et al. |
| 2015/0157052 A1 | 6/2015 | Ademe et al. |
| 2015/0245654 A1 | 9/2015 | Memari et al. |
| 2015/0335070 A1 | 11/2015 | Sears et al. |
| 2016/0157524 A1 | 6/2016 | Bowen et al. |
| 2016/0219938 A1 | 8/2016 | Mamoun et al. |
| 2017/0000188 A1 | 1/2017 | Nordskog et al. |
| 2017/0055576 A1 | 3/2017 | Beeson et al. |
| 2017/0065000 A1 | 3/2017 | Sears et al. |
| 2017/0164654 A1 | 6/2017 | Ademe |
| 2017/0238607 A1 | 8/2017 | Nordskog |
| 2017/0340008 A1 | 11/2017 | Sebastian et al. |
| 2018/0289074 A1* | 10/2018 | Tremblay .............. A24F 47/008 |
| 2019/0255266 A1 | 8/2019 | Henry et al. |

FOREIGN PATENT DOCUMENTS

| | | |
|---|---|---|
| WO | WO-98/46093 A1 | 10/1998 |
| WO | WO-02/098245 A1 | 12/2002 |
| WO | WO-2017/023589 A1 | 2/2017 |
| WO | WO-2017/027673 A1 | 2/2017 |

OTHER PUBLICATIONS

International Search Report and Written Opinion in PCT/US2019/050047, dated Dec. 12, 2019, 15 pages.

Non-Final Office Action in U.S. Appl. No. 15/892,151, dated Oct. 10, 2019, 20 pages.

Non-Final Office Action in U.S. Appl. No. 15/892,151, dated Jun. 1, 2020, 22 pages.

Non-Final Office Action in U.S. Appl. No. 16/131,785, dated Jul. 10, 2020, 12 pages.

* cited by examiner

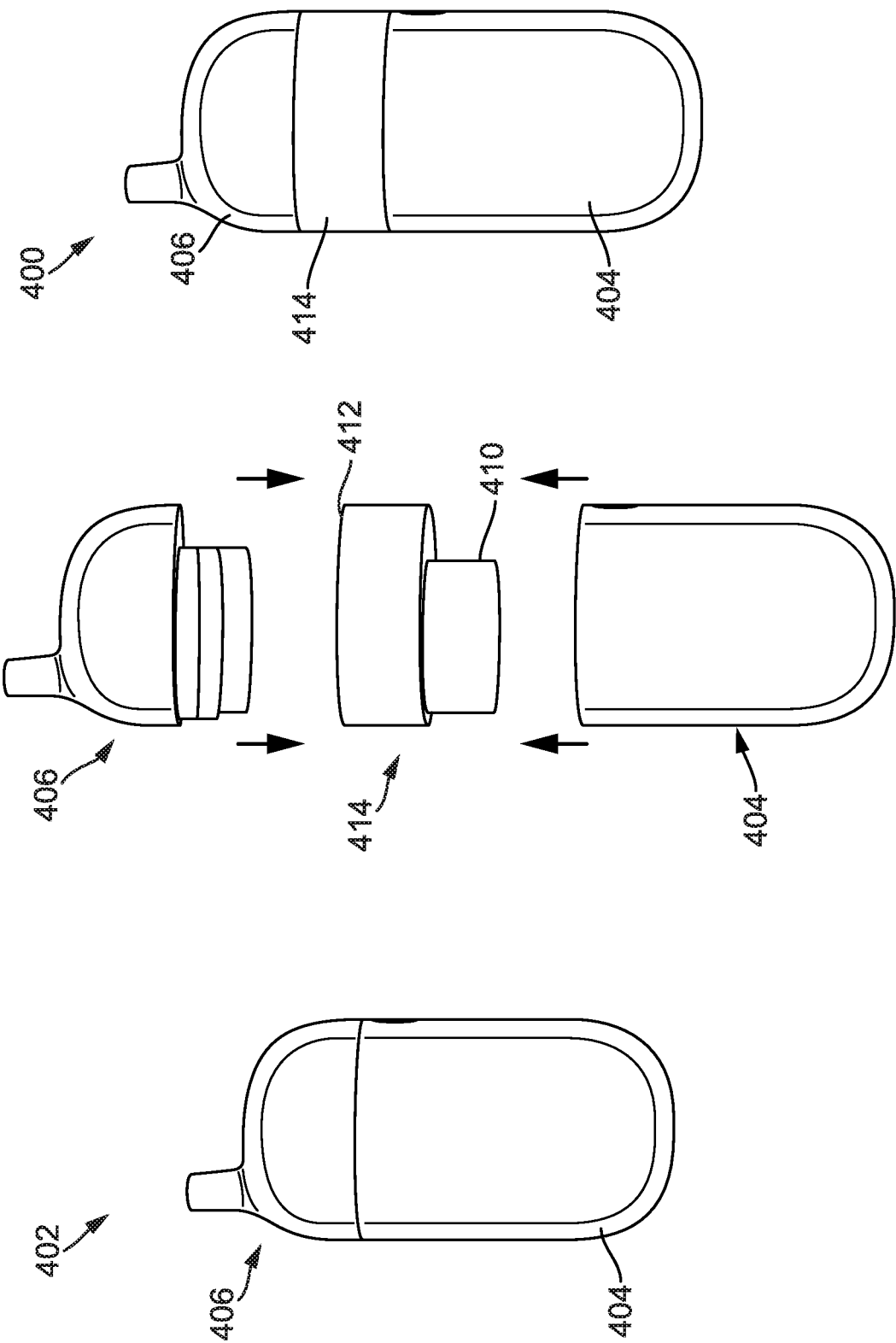

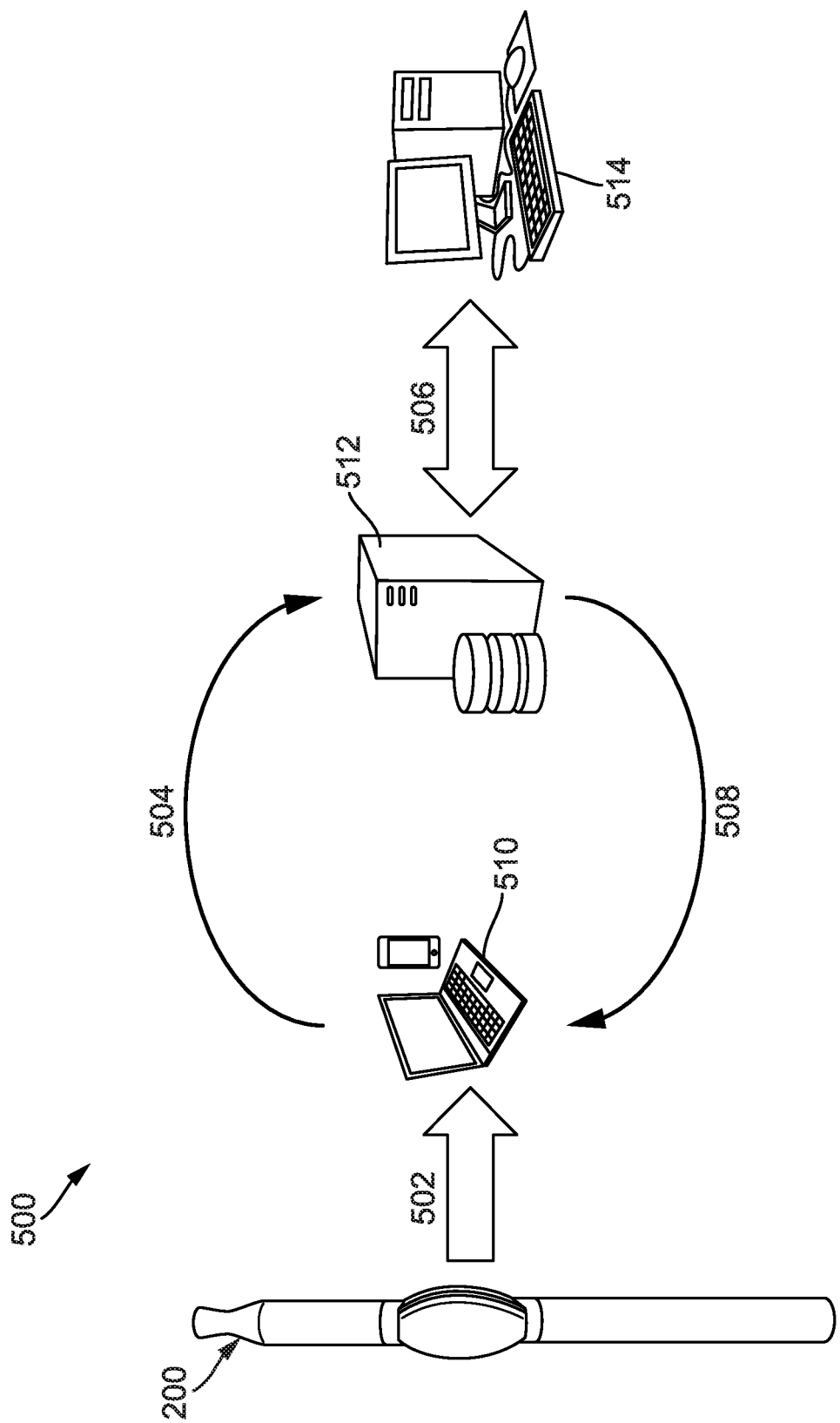

PRODUCT USE AND BEHAVIOR MONITORING INSTRUMENT

TECHNICAL FIELD

The present invention relates to aerosol delivery articles and uses thereof for yielding tobacco components or other materials in an inhalable form. The articles may be made or derived from tobacco or otherwise incorporate tobacco for human consumption. More particularly, the present invention relates generally to the field of electronic or electrically powered smoking articles.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. App. Pub. No. 2013/0255702 to Griffith Jr. et al., U.S. Pat. App. Pub. No. 2014/0000638 to Sebastian et al., U.S. Pat. No. 5,060,671 to Counts et al.; U.S. Pat. No. 9,016,274 to White; U.S. Pat. No. 9,078,474 to Thompson; U.S. Pat. App. Pub. No. 2014/0060554 to Collett et al., U.S. Pat. App. Pub. No. 2014/0096781 to Sears et al., U.S. patent application Ser. No. 13/826,929 to Ampolini et al., filed Mar. 14, 2013, and U.S. patent application Ser. No. 14/011,992 to Davis et al., filed Aug. 28, 2013, which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et. al, which are incorporated by reference in their entireties.

Popular electronic or electrically powered smoking articles (e.g., electronic cigarettes, E-cigarettes, etc.) (referred to herein collectively as "electronic smoking articles") often include a liquid storage component for storing aerosol precursor material (e.g., aerosol forming agent, liquid smoke, etc.), a vaporizing chamber with a heating coil attached for the aerosol precursor material to become vaporized therein, and a battery to power the device. The aerosol precursor material typically includes a mixture of propylene glycol, glycerin, nicotine, water and flavoring. Various electronic smoking articles have a single device which houses both the heating element and the aerosol precursor material in one unit, commonly referred to as a cartomizer.

Certain tobacco products that have employed electrical energy to produce heat for smoke or aerosol formation, and in particular, certain products that have been referred to as electronic cigarette products or electronic smoking articles, have been commercially available throughout the world. Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; GREEN SMOKE® by Green Smoke Inc. USA; GREENARETTE™ by Greenarette LLC; HALLIGAN™, HENDU™, JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC and VUSE® by R. J. Reynolds Vapor Company. Yet other electrically powered aerosol delivery devices, and in particular those devices that have been characterized as so-called electronic cigarettes, have been marketed under the tradenames BLU™; COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP® and SOUTH BEACH SMOKE™. In some of these electronic smoking articles, when the user inhales on the electronic smoking article, aerosol precursor material is 'pulled' from the reservoir into a vaporizing chamber using gravity and capillary in the wick. The aerosol precursor material is either adsorbed or resting on the vaporizer's heating apparatus and heated until it becomes vapor. The vapor is drawn away from the heated region of the device, where it subsequently cools and condenses into a high number density, generally sub-micron aerosol whereupon it then exits the device. The wick material can include any combination of silica, organic cotton, cellucotton rayon fibers, stainless steel, fiberglass, ceramic, and other materials with similar properties.

Currently, there are limited options for recording and understanding how individuals use electronic smoking articles. For example, in clinical trials, most attempts have tried to adapt technology used to measure combustible cigarette use (e.g., topography), use video recording of people using an electronic smoking article, or question individual users to recall how they used the electronic smoking article. These methods are limiting by constraining the individual user being monitored to a single location. Therefore, the recording and documentation of the usage occurs in "unrealistic" circumstances. In other words, the act of measuring usage impairs how the person uses the electronic smoking article by limiting the individual user to a specific testing location, and not under regular, day-to-day locations and usage. Further, what "traditional" (e.g., under current monitoring methods) topography actually measures does not directly relate to what occurs when people use electronic smoking articles. Traditional topography with electronic smoking articles focus on air volume and pressure created in the act of taking a puff. The instrumentation is built around pressure transducers and analog-to-digital converters that will translate puff pressure dynamics to collect and compute per-puff and per-cigarette summaries of puffing characteristics. The placement of the topography instrument is placed in between the electronic smoking article and the user. This placement changes how the user uses the product as compared to how they use it naturally. This interference might change the way users use the product during testing and not provide information that accurately represents how the user consumes the product in the real world. Also, using traditional topography the consumer/subject must sit, tethered to the traditional topography instrument in a laboratory environment, further impacting product use and behavior. Accordingly, it would be desirable to provide a device that can be retrofitted onto a variety of electronic smoking articles and can monitor and capture usage of an individual user and the electronic smoking article under normal conditions (e.g., usage by an individual on a day-to-day basis absent monitoring).

SUMMARY

Various example embodiments relate to a product use and behavior instrument and methods of using of such an instrument. According to a first set of embodiments, a product use and behavior instrument includes a housing defining a central compartment therein. A controller is positioned within the central compartment. The controller includes a first connector. The first connector is configured to operatively and removably couple the product use and behavior instrument to a battery element of an electronic smoking article. A second connector is configured to operatively and removably couple the product use and behavior instrument to a tank element of the electronic smoking article. A sensor circuit is structured to collect at least one use data characteristic of a smoking action. The smoking action is associated with use of at least one of the tank and battery element. Local memory is structured to store the at least one use data characteristic of the smoking action. A communication interface is structured to communicate the stored at least one use data characteristic of the smoking action to a remote computing device.

According to a second set of embodiments, an electronic smoking article is described. The electronic smoking article includes a tank element. The electronic smoking article further includes a battery element. The electronic smoking article further includes a product use and behavior instrument. The product use and behavior instrument includes a controller. The controller includes a first connector. The first connector removably and operatively connected to the battery element. A second connector is removably and operatively connected to the tank element. A sensor circuit is structured to collect at least one use data characteristic of a smoking action. The smoking action is associated with use of at least one of the tank and battery element. Local memory is structured to store the at least one use data characteristic of the smoking action. A communication interface is structured to communicate the stored at least one use data characteristic of the smoking action to a remote computing device.

In another set of embodiments, a method of capturing at least one use data characteristic of a smoking action is described. The method comprises providing an electronic smoking article to a user. The electronic smoking article includes a tank element. The electronic smoking article further includes a battery element. The electronic smoking article further includes a product use and behavior instrument. The product use and behavior instrument includes a controller. The controller includes a first connector. The first connector removably and operatively connected to the battery element. A second connector is removably and operatively connected to the tank element. A sensor circuit is structured to collect at least one use data characteristic of a smoking action. The smoking action is associated with use of at least one of the tank and battery element. Local memory is structured to store the at least one use data characteristic of the smoking action. A communication interface is structured to communicate the stored at least one use data characteristic of the smoking action to a remote computing device. A smoking action by the user is detected. The controller activates the sensor circuit. At least one use data characteristic of the smoking action is captured by the sensor circuit. The at least one use data characteristic of the smoking action is stored in the local memory.

These and other features, together with the organization and manner of operation thereof, will become apparent from the following detailed description when taken in conjunction with the accompanying drawings, wherein like elements have like numerals throughout the several drawings described below.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings. Exemplary embodiments of the present application will now be described, way of example only, with reference to the accompanying drawings, which are not necessarily drawn to scale, and wherein:

FIG. 4A is a perspective view of an assembled electronic smoking article, according to another example embodiment.

FIG. 4B is a perspective view of an unassembled product use and behavior monitoring instrument and electronic smoking article of FIG. 4A, according to a further example embodiment.

FIG. 4C is a perspective view of the assembled electronic smoking article with a product use and behavior monitoring instrument of FIG. 4B.

FIG. 5 is a schematic flow diagram illustrating a method for transmitting data from an electronic smoking article with a product use and behavior monitoring instrument, according to an example embodiment.

Figure 1:
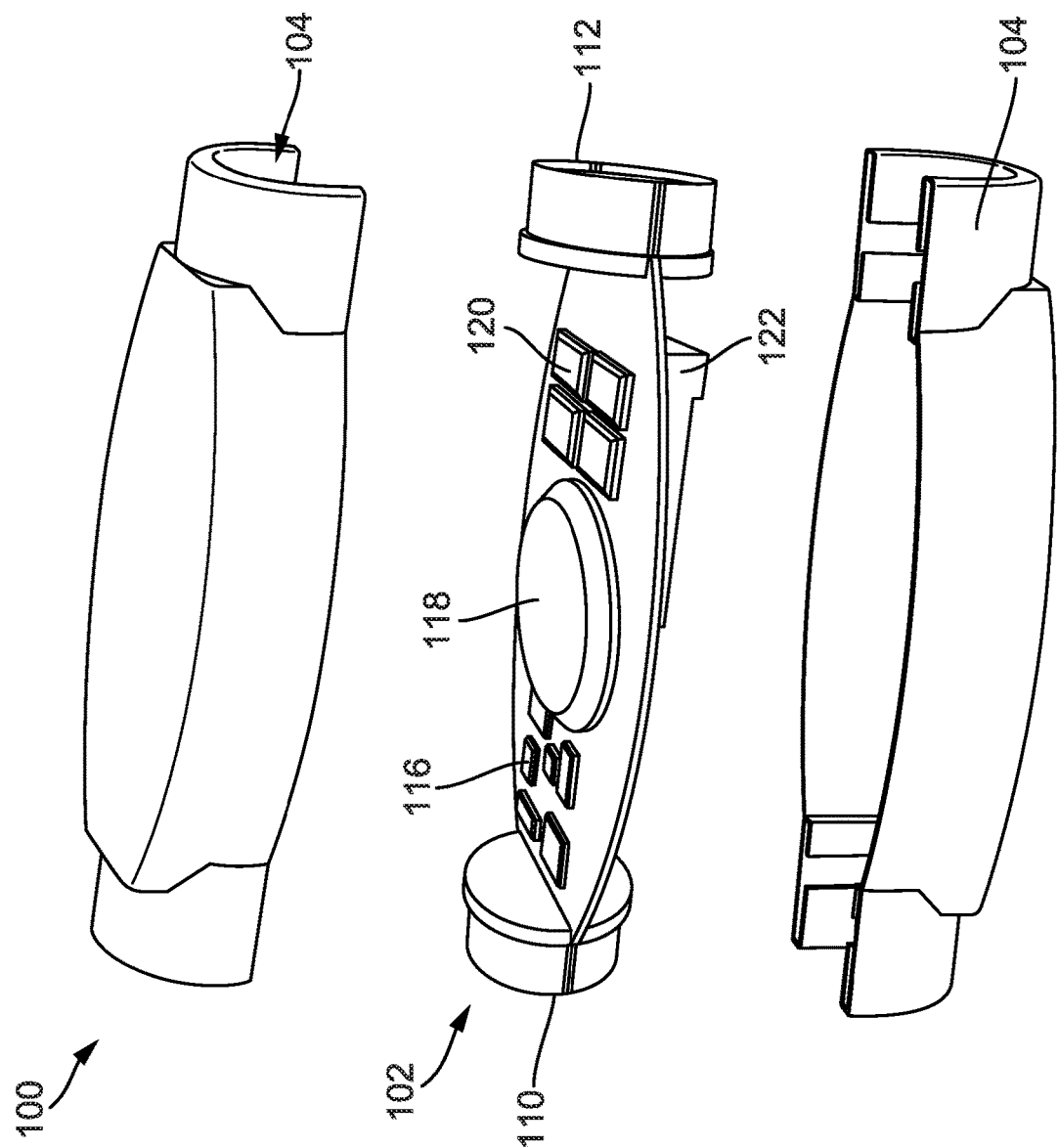
FIG. 1 is a perspective view of an unassembled product use and behavior monitoring instrument, according to an example embodiment.

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will be thorough and complete, will fully convey the scope of the disclosure to those skilled in the art, and will satisfy applicable legal requirements. Like numbers refer to like elements throughout. As used in this specification and the claims, the singular forms "a," "an," and "the" include plural referents unless the context clearly dictates otherwise.

DETAILED DESCRIPTION

Referring to the figures generally, a product use and behavior ("PUB") instrument is described. The PUB instrument is structured to record various aspects of electronic smoking article use including usage by a user of the electronic smoking article and how the electronic smoking article responds to that use. For example, the PUB instrument can record and detect battery activation of the electronic smoking article, battery characteristics (e.g., wattage, voltage, and resistance), location (e.g., global position), orientation of instrument, movement of instrument, temperature of airflow entering electronic smoking article, and sound of airflow entering electronic smoking article. In regard to user usage, the PUB instrument can measure use characteristics, moment-to-moment and patterns over periods of time (e.g., hourly, daily, weekly), puff behaviors (e.g., number, duration, inter-puff intervals, etc.), and changes in characteristic throughout a smoke session or over periods of time. Beneficially, the PUB instrument is structured for retrofitting onto a variety of electronic smoking articles, as it is adaptable to a wide variety of battery-tank or battery cartridge connections of the electronic smoking article. As used herein, the term "tank" refers to some or all of aerosol generating element of the electronic smoking article, including the cartridge, cartomizer, wicks, atomizers, heating elements, substrates, reservoirs, and similar elements. In some embodiments, the electronic smoking article is a heatless delivery system that utilizes mechanical nebulization.

Generally, the PUB instrument includes an array of sensors to record product use characteristics, an on-board memory to store collected data, an on-board rechargeable power source, a wireless (e.g., Bluetooth™) communication array to transfer data to an external storage location, a first connector for a tank end, and a second connector for a battery end. Once a PUB instrument is installed on electronic smoking article, data monitoring and collection may be triggered or continuous by activation and deactivation of the electronic smoking article. At the completion of a segment of data acquisition, the PUB instrument may synchronize with a wireless communication-compatible computing device (e.g., desktop, laptop, tablet, smartphone, etc.) and upload the data to a secure database. Data may be exportable to any statistical software package for further analysis or to task specific summarization software. As will be appreciated, the PUB instrument may be utilized for clinical and non-clinical research to capture and track use of an electronic smoking article use data for behavioral modelling, to track use, and to provide information about use patterns.

Unlike traditional clinical techniques (e.g., topography), the PUB instrument does not primarily use air movement to generate the values associated with puff dynamics due to the nature of the differences between combustible and electronic smoking article. Additionally, the PUB instrument is not in the pathway between the user (or clinical trial subject) and does not interfere with the normal functioning of the product and the experience the user has while using the electronic smoking article. Finally, the PUB device is completely portable and allows for the user to use the electronic smoking article in a clinic, laboratory, or ambulatory (anywhere outside of the clinic or laboratory) environment. This increases the likelihood that what the instrument records will be aligned with actual electronic smoking article use characteristics.

Referring to FIG. 1, a perspective view of an unassembled PUB instrument 100 is shown, according to an example embodiment. The PUB instrument 100 includes a controller 102 and a housing 104. In certain embodiments, the housing 104 includes a first outer shroud and a second outer shroud. The PUB instrument 100 monitors, records, and transmits a plurality of user usage data and electronic smoking article device data. The PUB instrument 100 is structured to have a form, size, and connectors that allow it to be adapted to interface with—without interfering with the operation of—a wide variety of electronic smoking articles (e.g., e-cigarette, pen, open and/or closed system "tank" product designs). As will be appreciated, the PUB instrument 100 may be used in both controlled and limited control environments, under supervision and unsupervised, durable, and in accordance with product safety standards for mobile research equipment.

The controller 102 includes a first end connector 110, a second end connector 112, a sensor array 116, a PUB battery 118, on-board memory 120, and an antenna 122. The controller 102 is structured to monitor, record, and store a plurality of data and characteristics of the user and electronic smoking article. The controller 102 is structured to have a size and connectors that will interface with a wide variety of electronic smoking article and interfere as little as physically possible with the intended form of an electronic smoking article. The controller 102 acquires real-time data related to characteristics of individual puff behaviors (e.g., number, duration, inter-puff intervals), change in puff characteristics from moment to moment, change in puff characteristics over a duration of time, and similar information. For example, captured puffing characteristics could include, but is not limited to, puff volume (ml), puff duration (s), number of puffs, number of sub-puffs, mean and peak flow (ml/s), mean and peak draft (ml/s), mean and peak resistance, mean and peak pressure drop (mmWg), inter puff interval (s), and time lit (s). The controller 102 may also acquire battery characteristics (e.g., wattage, voltage, and resistance), location, orientation of instrument, movement of instrument, temperature of airflow entering the electronic smoking article, and sound of airflow entering electronic smoking article. The controller 102 facilitates the storage of the data characteristics relating to moment-to-moment user use behaviors and patterns of usage across bouts of product interaction (e.g., hourly, daily, weekly). The controller 102, and associated elements, can be physically implemented on a circuit board.

The first end connector 110 includes a coupling element structured to removably couple to and interface with a battery end of an electronic smoking article. The electronic smoking article can be in a wide variety of different "forms," for example, a box style, a pen style, or an open system "tank" style product design. Each variety of an electronic smoking article can have different coupling mechanisms for attaching the battery to the tank. In some embodiments, one or more PUB instruments 100 (e.g., modules) may be used in a single electronic smoking article. In those embodiments, the first end connector 110 may be structured to couple with another module PUB instrument 100. As will be appreciated, the size and type of coupling element of the first end connector 110 is dependent upon the components that comprise the interior of a specific electronic smoking article. Exemplary connections are described below, in greater detail, in FIGS. 2A-4C.

The second end connector 112 includes a coupling element structured to removably couple to and interface with a tank (e.g., reservoir of smoking material) end of an electronic smoking article. An electronic smoking article can be in a wide variety of different "forms," for example, an electronic-cigarette, a pen, an open system "tank" product designs. Each variety of an electronic smoking article can have different coupling mechanisms for attaching the rechargeable battery to the tank. In some embodiments, one or more PUB instruments 100 (e.g., modules) may be used in a single electronic smoking article. In those embodiments, the second end connector 112 may be structured to couple with another PUB instrument 100. As will be appreciated, the size and type of coupling element of the second end connector 112 is dependent upon the components that comprise the interior of a specific electronic smoking article. The different connections are described below, in greater detail, in FIGS. 2A-4C.

The on-board memory 120 is structured to store data and characteristics collected by the sensor array 116. The on-board memory 120 may be flash memory or electrically erasable programmable read-only memory ("EEPROM") memory. The on-board memory 120 should provide sufficient memory capacity to allow storage of the highest estimated data load generated over a set period, for example, a seven day period. In some embodiments, the on-board memory 120 may be reset to null values and the on-board clock resynced once data is upload. In other embodiments, the on-board memory 120 is structured to maintain all data until the on-board memory 120 reaches capacity. The on-board memory 120 may store data in raw data format, time and date stamp it, and uses it to determine wattage values. As will be appreciated, the wattage values coupled with puff duration values may be used to generate a Total Particulate Matter ("TPM") constant for the estimated mouth-level exposure ("eMLE") of the aerosol measure. The data captured by the sensor array 116 is stored in the on-board memory 120 in both discrete individual data points and as part of a time and date-stamped cumulative record.

The PUB battery 118 includes an on-board, rechargeable battery. The PUB battery 118 may also be a rechargeable solid state battery. The PUB battery 118 powers the PUB instrument 100 and is structured to ensure that performance of data collection by the PUB instrument 100 will not affect the performance of the battery. The PUB battery 118 should be able to maintain a charge throughout the highest estimated level of subject use. In some embodiments, the PUB battery 118 will last for at least seven days without having to be re-charged. In some embodiments, the PUB battery 118 is recharged when the battery is recharged. In other embodiments, the PUB instrument 100 includes a charging port on the housing 104 that can charge the PUB battery 118. In some embodiments, the PUB instrument 100 does not have a PUB battery 118; instead the PUB instrument 100 draws power from the battery of the electronic smoking article.

The antenna 122 is structured to transmit collected by the sensor array 116 and stored by the on-board memory 120. The antenna 122 may be structured to upload data during the charging cycle of the electronic smoking article, during activation of the electronic smoking article device, continuously throughout the lifecycle of the electronic smoking article, or similar triggering events. In some embodiments, on-board memory 120 may be reset to null values and the on-board clock resynced once the data upload by the antenna 122 concludes. In some embodiments, the PUB instrument 100 uses Bluetooth™ technology to facilitate the transfer of data from the memory of the PUB instrument 100 to a secured location (e.g., a server location) through data transfer software (e.g., PC, iOS™, or Android™). With the transmission of the data over Bluetooth,™ the antenna 122 is designed to limit interfere with the aerosol generated as much as possible. In other embodiments, the antenna 122 has a wired interface that allows for a wired connection to the secured location through the data transfer software. Data security and integrity during migration from the antenna 122 of the PUB instrument 100 to the computer or smart device, to the database server may be maintained according to appropriate research data standards. In some embodiments, the data hosted in the secure database may be used to communicate with the PC and/or Smart Device (Smartphone and/or Tablet) to present additional information to the user of the PUB instrument 100.

The sensor array 116 is structured to monitor and record one or more data characteristics of the electronic smoking article and the user usage data. The sensor array 116 is structured to monitor and record a wide variety of user usage characteristics and data. The sensor array 116 can capture real-time data related to characteristics of individual use behaviors (e.g., number, duration, inter-puff intervals), how these characteristics change from moment to moment, and how battery characteristics, such as power (e.g., wattage), change moment to moment. The sensor array 116 may measure the time between when a puff is concluded (e.g., battery deactivation) and the initiation of the next puff (e.g., battery activation), also known as the inter-puff-interval ("IPI"). As will be appreciated, the puff statistics captured by the sensor array 116 can be used to capture puff, rapid-puffs, and sub-puff counts and duration values as well as IPI counts and duration values. In some embodiments, the sensor array 116 monitors and captures the activation of the battery—which aligns with the initiation of a puff—and measures the time that the battery is active to determine puff duration. In other embodiments, the sensor array 116 may record the conclusion of the puff when the battery is no longer active.

In regard to the electronic smoking article, the sensor array 116 may include specific sensors to detect battery activation of the electronic smoking article, battery characteristics (e.g., wattage, voltage, current, and resistance), or duration of battery use (e.g., length of smoke session). As will be appreciated, the data captured by the sensor array 116 is stored in the on-board memory 120 in both discrete individual data points and as part of a time and date-stamped cumulative record.

In some embodiments, the sensor array 116 includes hardware sensors that track the position of the electronic smoking article while being used. For example, a 9-axis gyroscope is used to capture the orientation of the PUB instrument 100, an accelerometer to capture the movement of the PUB instrument 100, or a global position system ("GPS") to capture the location of the PUB instrument 100. In such embodiments, the position tracker(s) can be used to generate data concerning the location of the electronic smoking article in regards to the location relationship between the battery-end and the tank-end of the electronic smoking article. Beneficially, recording this location relationship allows for the researchers to determine how the user was holding the electronic smoking article while performing a puff. Determining if the user was holding the electronic smoking article while sitting in a manner similar to a traditional cigarette vs. smoking the electronic smoking article while lying on the couch with the battery above the tank provides more information regarding regular use of the electronic smoking article and can provide details toward tank leakage and mal-/miss-functioning of the electronic smoking article product.

The sensor array 116 may include hardware sensors that detect changes in the ambient temperature within airway ports of the electronic smoking article. The temperature changes may be used to identify when a puff is initiated and ongoing use of the electronic smoking article. In some embodiments, the PUB instrument 100 may include hardware sensors that detect the speed of movement of the PUB instrument 100 from one position to another. In those embodiments, linear acceleration of the PUB instrument 100 is measured in relation to use/non-use to identify the beginning of a period of product use. In other embodiments, the PUB instrument 100 may include hardware sensors that record the frequency of the sound of air passing through dedicated airway ports on the PUB instrument 100. In such embodiments, the use of passive acoustic measurements may provide information to understand puff velocity and the general shape of individual puff characteristics.

The PUB instrument 100 may also include hardware sensors that track and record events measured by other components that make up the PUB instrument 100. Beneficially, this tracking is date and time stamped such that all recorded events form a cumulative record. The cumulative record is trackable and exportable to any statistical software package for further analysis or to task specific summarization software. In other embodiments, the PUB instrument 100 may include a photo-, mechanical-, and/or pressure sensor that will detect if the PUB instrument 100 has been removed from the battery and/or tank end of the electronic smoking article.

In some embodiments, the PUB instrument 100 includes a toggle function on the controller 102. The toggle function can turn on, turn off, limit, or alter one or more data characteristics monitoring and recorded by the PUB instrument 100. For example, the toggle function may limit the total puffs generated (e.g., in terms of duration, number, or a combination of both) over a specific period of time (e.g., minutes/hours/days/weeks, etc.) in order to limit the number of uses of the electronic smoking article. In other embodiments, the PUB instrument 100 includes a single activation button that can be used to trigger or mark events (e.g., date/time/location) that occur during the course of usage of the electronic smoking article. In some embodiments, the PUB instrument 100 includes a screen (e.g., LCD) inserted on the housing 104. The screen displays the status of any of the events that the PUB instrument 100 records or manages. The screen may also facilitate the user to adjust the data the sensor array monitors and records, for example through the toggle function. The user may use the screen to select an "off" option for one or more data characteristics collected, for example, location of the user throughout usage of the PUB instrument 100.

A PUB instrument 100 may also include an identifier related to the structure and characteristics of the PUB instrument 100. The identifier is updatable for each user throughout the use of the PUB instrument 100. As will be appreciated, this would allow a user to switch between a clinical (e.g., data captured for a third party's analysis) or non-clinical (e.g., data captured for the user's analysis) study. The identifier can be incorporated into the data set to allow for alignment of data type (e.g., clinical, non-clinical, specific user, PUB instrument 100 type) a data source. Additionally, the identifiers may be encoded into the PUB instrument 100 and visually apparent through an embossed portion of—or affixed by label to—the housing 104 of the PUB instrument 100. In some embodiments, the sensor array 116 may include an access control through biometric security sensor such as, for example, a fingerprint sensor to detect fingerprint characteristics. In those embodiments, the use of the electronic smoking article and/or the data characteristic collection may only occur is the fingerprint sensor captures a fingerprint from an authorized user (e.g., associated with the PUB instrument).

In certain embodiments, the PUB instrument 100 is configured as a series of modules. A single module PUB instrument 100 may be located between the battery end and tank end of an electronic smoking article. A single module PUB instrument 100 may be structured to monitor and record a single or multiple data or characteristics. Multiple module PUB instruments 100 may be connected along the electronic smoking article to monitor and record a single or multiple data or characteristics. As will be appreciated, with module PUB instruments 100 an electronic smoking article can be tailored to capture a specific subset of data and characteristics. For example, a user may want to utilize the PUB instrument 100 to capture data characteristics, but not allow the transmission or capture of any location data. Therefore, the user's electronic smoking article could include module PUB instruments 100 that monitor and record data or characteristics unrelated to location. In some embodiments, the PUB instrument 100 includes a chip that is structured to interface on an electronic smoking article and collect least one use data characteristic.

As will be appreciated, data collected by the sensor array 116 can be input into a graphical-based software program for summary and pattern recognition of electronic smoking article use over specific periods of time. The software may import raw data exported from database on a per-user/per-trial basis. The data may be processed for summarizing and applying algorithms for computing discrete product use elements, product use rate and/or patterns, and the eMLE of the aerosol measure. Within the software program, information associated with the specific electronic smoking article under evaluation (e.g., TPM data values) needed to perform analytics are modifiable. Data generated by this process may be uploaded to the PUB instrument 100 database. As will be appreciated, data imported and results exported meet standards for data security and integrity. In other embodiments, the data collected by the sensor array 116 is sent to a task specific summarization software.

Figure 2C:
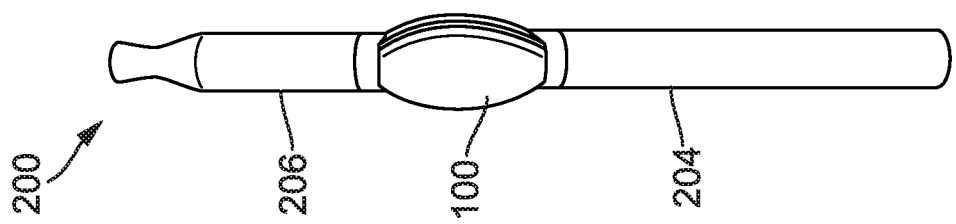
FIG. 2C is a perspective view of the assembled electronic smoking article with a product use and behavior monitoring instrument of FIG. 2B.
Figure 2B:
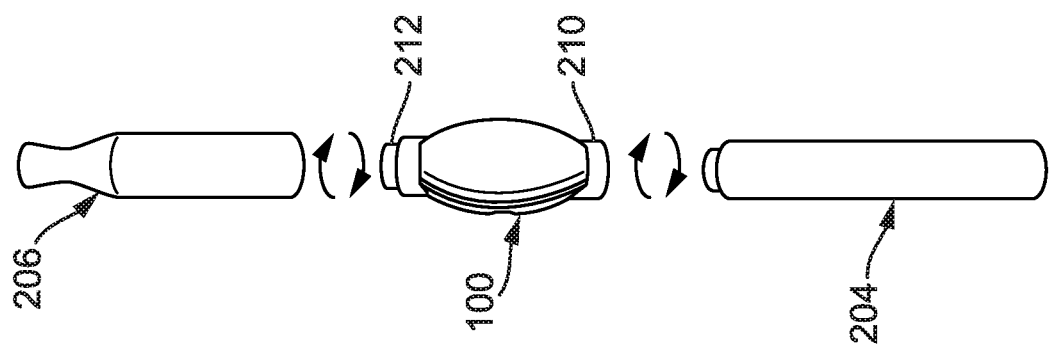
FIG. 2B is a perspective view of an unassembled product use and behavior monitoring instrument and electronic smoking article of FIG. 2A, according to a further example embodiment.
Figure 2A:
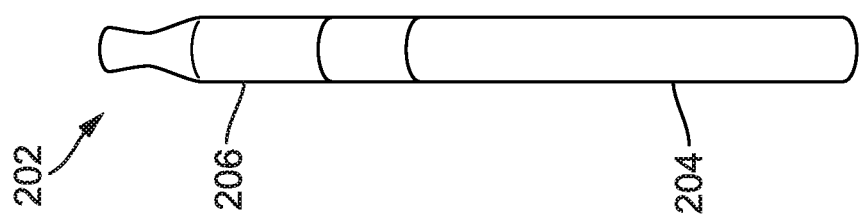
FIG. 2A is a perspective view of an assembled electronic smoking article, according to another example embodiment.

Referring to FIG. 2A, a perspective view of an assembled electronic smoking article 202 is shown, according to an example embodiment. The electronic smoking article 202 includes a battery 204 and a cylindrical reservoir 206 containing a liquid or other smoking material. The battery 204 is removably coupled to the reservoir 206 via complementary torsion (e.g., twist) interfaces on an end of the battery 204 and an end of the reservoir 206. As will be appreciated, a user of the electronic smoking article 202 can twist off the battery 204 from reservoir 206 to replace either component, to charge the battery 204, for maintenance purposes, or similar actions. In some embodiments, the electronic smoking article 202 has a light-emitting diode ("LED") indicator end on the battery 204. The LED indicator end will simulate a traditional cigarette lit end, indicating when the electronic smoking article is working. A mouth end on the reservoir 206 allows for the user to breathe into or draw from the electronic smoking article 202, drawing in air through the battery 204 to the liquid in the reservoir 206, and, ultimately the mouth end to the user. In one embodiment, inhalation to draw in air starts the vaporization process. Alternatively, activation of a circuit closure (mechanical or optical) starts the vaporization process.

In contrast to more conventional cigarettes, the byproduct generated by the electronic smoking article 202 is not a smoke, but rather an aerosol or a vapor resulting from the volatilization or vaporization of certain components incorporated therein. For example, inhalable substances can be in the particulate matter fraction of the aerosol with some aerosol components in the true vapor phase or inhalable substances can be in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "vaporized liquid" as used herein is meant to include vapors, gases, and particles, i.e., aerosols of a form or type suitable for human inhalation, whether or not visible, and whether or not of a form that might be considered to be smoke-like.

The reservoir 206 contains a liquid that is vaporized and delivered to the user. In some embodiments, the liquid includes substances such as, for example nicotine (which may include tobacco-specific nitrosamines (TSNAs), aldehydes, or metals), propylene glycol, glycerin, water, flavor agents, or any other suitable material that can be used to be vaporized. In particular embodiments, the liquid is a combination of nicotine, propylene glycol, and glycerin. Further, volatile organic compounds (VOCs) or tobacco alkaloids may be generated during the heating process. The reservoir is not limited to a particular size and can be opaque or transparent so that a user can view the liquid therein.

FIG. 2B illustrates a perspective view of an unassembled PUB instrument 100 and the electronic smoking article of FIG. 2A, according to an example embodiment. As shown in FIG. 2B, the PUB instrument 100 includes a first end connector 210 structured for torsional interface with the battery 204 end of the electronic smoking article 202. The PUB instrument further includes a second end connector 212 structured for torsional (e.g., twist) interface with the reservoir 206 end of the electronic smoking article 202. As will be appreciated, the PUB instrument 100 may include one or more of the components and sensor array 116 described above. While only one PUB instrument 100 is shown in FIG. 2B, in some embodiments, one or more PUB instruments 100 (e.g., modules) may be used in the electronic smoking article 202. In those embodiments, the first end connector 210, the second end connector 212, or both may be structured to couple with another PUB instrument 100. In some embodiments, the housing 104 of the PUB instrument 100 are altered to better fit the form of the electronic smoking article 202. As will be appreciated, the size and type of coupling element of the first end connector 110 is dependent upon the components that comprise the interior of the electronic smoking article 202.

Turning to FIG. 2C, a perspective view of the assembled electronic smoking article 202 with a PUB instrument 100 (the combination referred herein as the "PUB delivery system" 200) of FIG. 2B is shown, according to an example embodiment. The PUB delivery system 200 has the same general form and structure of the original electronic smoking article 202. The PUB instrument 100 has a size and form that is structured to minimally interfere physically with the intended form of the electronic smoking article 202. The components of the PUB instrument 100 ensure that the performance and use of the PUB delivery system 200 is substantially similar to the performance and use of the electronic smoking article 202.

Figure 3C:
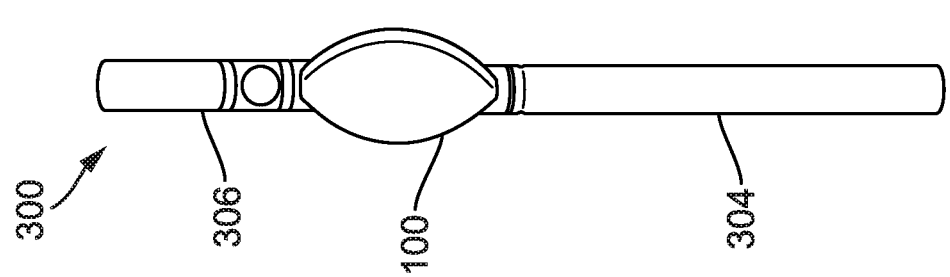
FIG. 3C is a perspective view of the assembled electronic smoking article with a product use and behavior monitoring instrument of FIG. 3B.
Figure 3B:
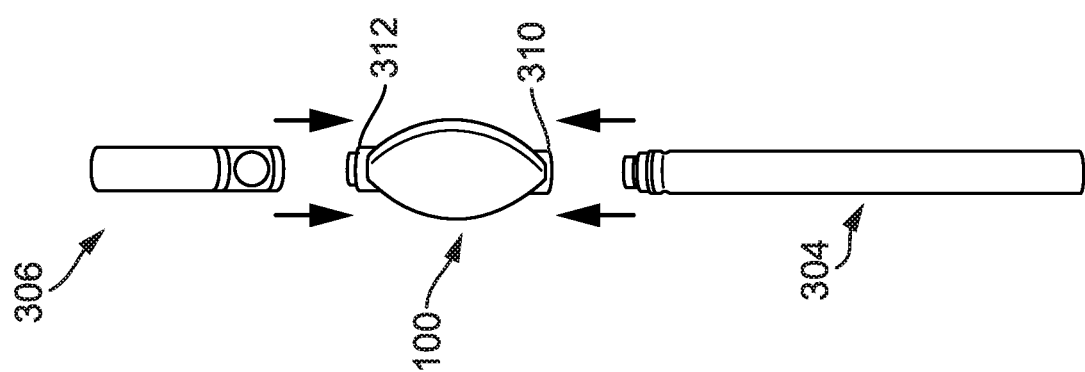
FIG. 3B is a perspective view of an unassembled product use and behavior monitoring instrument and electronic smoking article of FIG. 3A, according to yet another example embodiment.
Figure 3A:
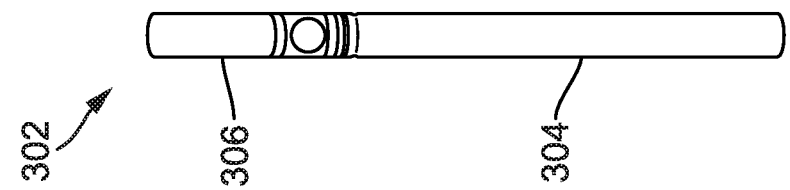
FIG. 3A is a perspective view of an assembled electronic smoking article, according to an example embodiment.

Referring to FIG. 3A, a perspective view of an assembled electronic smoking article 302 is shown, according to an example embodiment. The electronic smoking article 302 is similar to the electronic smoking article 202. A difference between the electronic smoking article 302 and the electronic smoking article 202 is the coupling interface between the battery 304 and the reservoir 306 of the electronic smoking article 302 is the interlocking interface. The electronic smoking article 302 includes a battery 304 and a cylindrical reservoir 306 containing a liquid or other smoking material. The battery 304 is removably coupled to the reservoir 306 via complementary interlocking (e.g., snap-fit) interfaces on an end of the battery 304 and an end of the reservoir 306. As will be appreciated, a user of the electronic smoking article 302 can be pushed to snap-fit the battery 304 to the reservoir 306 or pulled apart to replace either component, to charge the battery 304, for maintenance purposes, or similar actions. In some embodiments, the electronic smoking article 302 has an LED indicator end on the battery 304. The LED indicator end will simulate a traditional cigarette lit end, indicating when the electronic smoking article is working. A mouth end on the reservoir 306 allows for the user to breathe into the electronic smoking article 302, drawing in air through the battery 304 to the liquid in the reservoir 306, and, ultimately the mouth end to the user. In one embodiment, inhalation to draw in air starts the vaporization process. Alternatively, activation of a circuit closure (mechanical or optical) starts the vaporization process.

As noted previously, the byproduct generated by the electronic smoking article 302 is not a smoke, but rather an aerosol or a vapor resulting from the volatilization or vaporization of certain components incorporated therein. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). The reservoir 306 contains a liquid that is vaporized and delivered to the user.

FIG. 3B illustrates a perspective view of an unassembled PUB instrument 100 and the electronic smoking article of FIG. 3A is shown, according to an example embodiment. As shown in FIG. 3B, the PUB instrument 100 includes a first end connector 310 structured for interlocking interface with the battery end of the electronic smoking article 302. The PUB instrument further includes a second end connector 312 structured for interlocking interface with the reservoir end 306 of the electronic smoking article 302. As will be appreciated, the PUB instrument 100 may include one or more of the components and sensor array 116 described above. While only one PUB instrument 100 is shown in FIG.

3B, in some embodiments, one or more PUB instruments 100 (e.g., modules) may be used in the electronic smoking article 302. In those embodiments, the first end connector 310, the second end connector 312, or both may be structured to couple with another PUB instrument 100. In some embodiments, the housing 104 of the PUB instrument 100 are altered to better fit the form of the electronic smoking article 302. As will be appreciated, the size and type of coupling element of the first end connector 110 is dependent upon the components that comprise the interior of the electronic smoking article 302.

Turning to FIG. 3C, a perspective view of the assembled electronic smoking article 302 with a PUB instrument 100 (the combination referred herein as the "PUB delivery system" 300) of FIG. 3B is shown, according to an example embodiment. The PUB delivery system 300 has the same general form and structure of the original electronic smoking article 302. The PUB instrument 100 has a size and form that is structured to minimally interfere physically with the intended form of the electronic smoking article 302. The components of the PUB instrument 100 ensure that the performance and use of the PUB delivery system 300 is substantially similar to the performance and use of the electronic smoking article 302.

Referring to FIG. 4A, a perspective view of an assembled electronic smoking article 402 is shown, according to another example embodiment. The electronic smoking article 402 is similar to the electronic smoking article 302. A difference between the electronic smoking article 402 and the electronic smoking article 302 is the construction of the battery 404 and the reservoir 406 of the electronic smoking article 402. The electronic smoking article 402 includes a battery 404 and an oblong reservoir 406 containing a liquid or other smoking material. The battery 404 is removably coupled to the reservoir 406 via complementary interlocking (e.g., snap-fit) interfaces on an end of the battery 404 and an end of the reservoir 406. As will be appreciated, a user of the electronic smoking article 402 can be pushed to snap-fit the battery 404 to the reservoir 406 or pulled apart to replace either component, to charge the battery 404, for maintenance purposes, or similar actions. In some embodiments, the electronic smoking article 402 has an LED indicator end on the battery 404. The LED indicator end will simulate a traditional cigarette lit end, indicating when the electronic smoking article is working. A mouth end on the reservoir 406 allows for the user to breathe into the electronic smoking article 402, drawing in air through the battery 404 to the liquid in the reservoir 406, and, ultimately the mouth end to the user. In one embodiment, inhalation to draw in air starts the vaporization process. Alternatively, activation of a circuit closure (mechanical or optical) starts the vaporization process.

As noted previously, the byproduct generated by the electronic smoking article 402 is not a smoke, but rather an aerosol or a vapor resulting from the volatilization or vaporization of certain components incorporated therein. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). The reservoir 406 contains a liquid that is vaporized and delivered to the user.

Turning to FIG. 4B, a perspective view of an unassembled PUB instrument 414 and the electronic smoking article of FIG. 4A is shown, according to an example embodiment. The PUB instrument 414 is similar to the PUB instrument 100. A difference between the PUB instrument 414 and the PUB instrument 100 is the shape of the housing 104 of the PUB instrument 414 and the first and second end connector (410, 412). As shown in FIG. 4B, the PUB instrument 414 includes a first end connector 410 structured for interlocking interface with the battery end of the electronic smoking article 402. The PUB instrument further includes a second end connector 412 structured for interlocking interface with the reservoir end 406 of the electronic smoking article 402. While the PUB instrument 414 has a different shape, the PUB instrument 414 may include one or more of the components and sensor array 116 described above. While only one PUB instrument 414 is shown in FIG. 4B, in some embodiments, one or more PUB instruments 414 (e.g., modules) may be used in the electronic smoking article 402. In those embodiments, the first end connector 410, the second end connector 412, or both may be structured to couple with another PUB instrument 414. In some embodiments, the housing 104 of the PUB instrument 414 are altered to better fit the form of the electronic smoking article 402. As will be appreciated, the size and type of coupling element of the first end connector 110 is dependent upon the components that comprise the interior of the electronic smoking article 402.

As illustrated in FIG. 4C, the electronic smoking article 402 is assembled with a PUB instrument 414 (the combination referred herein as the "PUB delivery system" 400) of FIG. 4B. The PUB delivery system 400 has the same general form and structure of the original electronic smoking article 402. The PUB instrument 414 has a size and form that is structured to minimally interfere physically with the intended form of the electronic smoking article 402. The components of the PUB instrument 414 ensure that the performance and use of the PUB delivery system 400 is substantially similar to the performance and use of the electronic smoking article 402.

Referring to FIG. 5, a schematic flow diagram illustrating a method 500 for transmitting data from a PUB delivery system 200 is shown, according to an example embodiment. The method 500 is described in connection with recorded data on a PUB delivery system 200 being synced to a user computing system 510 (e.g., laptop, tablet, desktop, mobile computing device, etc.), a secure server system 512 (e.g., database, cloud storage, etc.), and a clinical computing system 514. The PUB delivery system 200 can be a similar PUB delivery system, for example, to the PUB delivery systems (300, 400) of FIGS. 3C and 4C. As will be appreciated, data and results exported and imported meets the standards for clinical data security and integrity.

The method 500 begins at 502 with the PUB delivery system 200 synchronizing data stored on the on-board memory 120 of the PUB delivery system 200 to a user computing system 510 associated with the user. The data synchronization can occur using the antenna 122 of the PUB instrument 100. The data synchronization can be triggered, for example, by the charging cycle of a component of the PUB delivery system 200, during activation of the PUB delivery system 200, continuously throughout the lifecycle of the PUB delivery system 200, or a similar triggering event. In some embodiments, the PUB delivery system 200 uses Bluetooth™ technology to facilitate the transfer of data from the memory of the PUB delivery system 200 to the user computing system 510 through data transfer software (e.g., PC, iOS™, or Android™). In other embodiments, the PUB delivery system 200 has a wired interface that allows for a wired connection to the user computing system 510 through the data transfer software.

The data synchronization may include data related to moment-to-moment use behaviors and patterns of usage behaviors across periods of product interaction (e.g., hourly, daily, weekly) by the user. The PUB delivery system 200 acquires real-time data related to characteristics of individual use (puff) behaviors (e.g., number, duration, inter-puff intervals), how these characteristics change from moment to moment, and how battery characteristics change moment to moment. Using pre-determined and established TPM rates, multiple a eMLEs of the PUB delivery system 200 aerosol can be determined. In some embodiments, the conclusion of the data synchronization causes the data stored on the on-board memory 120 to be reset to null values and the on-board clock to be resynced.

At 504, the data transferred from the user computing system 510 is transferred to the secure server system 512 over the network. The network may include, for example, the Internet, cellular networks, proprietary cloud networks, and similar infrastructures. In some embodiments, the transfer is maintained according to appropriate research data standards.

At 506, the data stored on the secure server system 512 is accessed by a clinical computing system 514. One or more clinical computing system 514 may have access to the secure data on the secure server system 512. As will be appreciated, data accessed by the clinical computing system 514 can be input into a graphical-based software program for summary and pattern recognition of electronic smoking article 202 use over specific periods of time. The software may import raw data exported from database on a per-user/per-trial basis. The data may be processed for summarizing and applying algorithms for computing discrete product use elements, product use rate and/or patterns, and the eMLE. Within the software program, information associated with the specific electronic smoking article 202 under evaluation (e.g., TPM data values) needed to perform analytics are modifiable. Data generated by this process may be uploaded both onto the secure server system 512.

In some embodiments, the data hosted in the secure server system 512 may be used to communicate 508 with the user computing system 510 to present additional information to the PUB delivery system 200. Such information may comprise, for example, software updates for the PUB instrument, security updates for data transfer and storage, alteration of functions, addition of functions, data presentation to the user, statistics of user usage, additional control functions, authorized user updates, data storage updates, etc. For example, to cause the PUB delivery system to monitor and capture data related to a specific characteristic.

It should be noted that any use of the term "example" herein to describe various embodiments is intended to indicate that such embodiments are possible examples, representations, and/or illustrations of possible embodiments (and such term is not intended to connote that such embodiments are necessarily extraordinary or superlative examples). Further, while multiple embodiments describe various dimensions and connections of the PUB instrument, it is anticipated that the PUB instrument may have a connection cross-section of a wide variety of target shapes and sizes.

As utilized herein, the term "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed (e.g., within plus or minus five percent of a given angle or other value) are considered to be within the scope of the invention as recited in the appended claims. The term "approximately" when used with respect to values means plus or minus five percent of the associated value.

The terms "coupled" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other example embodiments, and that such variations are intended to be encompassed by the present disclosure.

The computer readable program code (e.g., identification code) embodied on a processing circuit may be transmitted using any appropriate medium, including but not limited to wireless, wireline, optical fiber cable, Radio Frequency (RF), or the like, or any suitable combination of the foregoing. In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

It is important to note that the construction and arrangement of the various example embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Additionally, features from particular embodiments may be combined with features from other embodiments as would be understood by one of ordinary skill in the art. Other substitutions, modifications, changes and omissions may also be made in the design, operating conditions and arrangement of the various example embodiments without departing from the scope of the present invention.

Additionally, the format and symbols employed are provided to explain the logical steps of the schematic diagrams and are understood not to limit the scope of the methods illustrated by the diagrams. Although various arrow types and line types may be employed in the schematic diagrams, they are understood not to limit the scope of the corresponding methods. Indeed, some arrows or other connectors may be used to indicate only the logical flow of a method. For instance, an arrow may indicate a waiting or monitoring period of unspecified duration between enumerated steps of a depicted method. Additionally, the order in which a particular method occurs may or may not strictly adhere to the order of the corresponding steps shown. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

What is claimed is:

1. A product use and behavior instrument comprising:
a housing comprising a first housing end and a second housing end disposed away from the first housing end, the housing defining a central compartment between the first housing end and the second housing end; and
a controller positioned within the central compartment of the housing, the controller comprising:
a first connector adjacent the first housing end, the first connector configured to operatively and removably couple the product use and behavior instrument to a battery element of an electronic smoking article;
a second connector adjacent the second housing end, the second connector configured to operatively and removably couple the product use and behavior instrument to a tank element of the electronic smoking article;
a sensor circuit structured to capture at least one use data characteristic of a smoking action when the first connector is coupled to the battery element and the second connector is coupled to the tank element, wherein the smoking action is associated with the use of at least one of the tank element and the battery element;
a battery configured to power the instrument;
local memory structured to store the at least one use data characteristic of the smoking action; and
a communication interface structured to communicate the stored at least one use data characteristic of the smoking action to a remote computing device.

2. The product use and behavior instrument of claim 1, wherein the first connector and the second connector comprise torsion coupling members.

3. The product use and behavior instrument of claim 1, wherein the first connector and the second connector comprise press coupling members.

4. The product use and behavior instrument of claim 1, wherein the at least one use data characteristic of the smoking action includes an activity component and a time component.

5. The product use and behavior instrument of claim 4, wherein the activity component comprises at least one of puff number, puff duration, and inter-puff interval, and wherein the time component comprises at least one of activity time, activity duration, and activity period.

6. The product use and behavior instrument of claim 4, wherein the activity component comprises at least one of battery current, battery voltage, battery resistance, orientation, temperature of air flow, air flow pressure, and
wherein the time component comprises at least one of activity time, activity duration, and activity period.

7. The product use and behavior instrument of claim 1, wherein the sensor circuit begins capturing the at least one use data characteristic of the smoking action upon detection of a change in ambient temperature within the product use and behavior instrument.

8. The product use and behavior instrument of claim 1, wherein the controller further comprises a position sensor circuit, the position sensor circuit structured to provide information regarding positioning and orientation of the first housing end and the second housing end during the smoking action.

9. The product use and behavior instrument of claim 1, wherein the controller further comprises a toggle button, the toggle button is structured to alter operation of at least one of the sensor circuit, the local memory, and the communication interface.

10. The product use and behavior instrument of claim 1, wherein the at least one use data characteristic of the smoking action includes an identifier, the identifier including at least one of a clinical data type, a non-clinical data type, and a user identifier.

11. The product use and behavior instrument of claim 1, wherein the communication interface is structured to communicate the at least one use data characteristic of the smoking action stored in the local memory to a receiving computing system when the product use and behavior instrument is within range of the receiving computing system.

12. The product use and behavior instrument of claim 1, further comprising a power source.

13. The product use and behavior instrument of claim 1, further comprising a pressure sensor configured to measure a flow of air.

14. The product use and behavior instrument of claim 1, further comprising a rechargeable solid state battery.

15. The product use and behavior instrument of claim 1, wherein the sensor circuit captures the use of at least one of the tank element and the battery element only when the battery element of the electronic smoking article is active.

16. The product use and behavior instrument of claim 1, further comprising a charging port positioned on the housing and coupled to the battery, the charging port configured to charge the battery when the charging port is coupled to a power source.

17. The product use and behavior instrument of claim 1, wherein the first connector and the second connector are the same type of connector.

18. An electronic smoking article, comprising:
a tank element;
a battery element; and
a product use and behavior instrument comprising:
a housing comprising a first housing end and a second housing end disposed away from the first housing end, the housing defining a central compartment between the first housing end and the second housing end; and
a controller positioned within the central compartment of the housing, the controller comprising:
a first connector adjacent the first housing end, the first connector removably and operatively connected to the battery element;
a second connector adjacent the second housing end, the second connector removably and operatively connected to the tank element;
a sensor circuit structured to capture at least one use data characteristic of a smoking action when the first connector is coupled to the battery element and the second connector is coupled to the tank element, wherein the smoking action is associated with the use of at least one of the tank element and the battery element;

a battery configured to power the instrument;

local memory structured to store the at least one use data characteristic of the smoking action; and a communication interface structured to communicate the stored at least one use data characteristic of the smoking action to a remote computing device.

19. The electronic smoking article of claim 18, wherein the first connector and the second connector comprise a torsion coupling member.

20. The electronic smoking article of claim 18, wherein the first connector and the second connector comprise press a coupling member.

21. The electronic smoking article of claim 18, wherein the sensor circuit begins capturing the at least one use data characteristic of the smoking action upon detection of a change in ambient temperature within the electronic smoking article.

22. The electronic smoking article of claim 18, wherein the controller further comprises a position sensor circuit, the position sensor circuit structured to provide information regarding positioning and orientation of battery element and the tank element during the smoking action.

23. The electronic smoking article of claim 18, wherein the at least one use data characteristic of the smoking action includes an activity component and a time component.

24. The electronic smoking article of claim 18, wherein the activity component comprises at least one of puff number, puff duration, and inter-puff interval, and wherein the time component comprises at least one of activity time, activity duration, and activity period.

25. A method for capturing at least one use data characteristic of a smoking action, comprising:

providing an electronic smoking article to a user, the electronic smoking article comprising:

a tank element;

a battery element; and a product use and behavior instrument comprising:

a housing comprising a first housing end and a second housing end disposed away from the first housing end, the housing defining a central compartment between the first housing end and the second housing end; and a controller positioned within the central compartment of the housing, the controller comprising:

a first connector adjacent the first housing end, the first connector removably and operatively connected to the battery element;

a second connector adjacent the second housing end, the second connector removably and operatively connected to the tank element;

a sensor circuit structured to capture at least one use data characteristic of a smoking action when the first connector is coupled to the battery element and the second connector is coupled to the tank element, wherein the smoking action is associated with the use of at least one of the tank element and the battery element;

a battery configured to power the instrument;

local memory structured to store the at least one use data characteristic of the smoking action; and a communication interface structured to communicate the stored at least one use data characteristic of the smoking action to a remote computing device;

detecting the smoking action by the user;

activating the sensor circuit by the controller;

capturing the at least one use data characteristic of the smoking action with the sensor circuit; and storing the at least one use data characteristic of the smoking action in the local memory.

26. The method of claim 25, further comprising transmitting the at least one use data characteristic stored in local memory to a receiving computing system via the communications interface.

27. The method of claim 25, wherein detecting the smoking action by the user comprises detecting, by the sensor circuit, a change in ambient temperature within the electronic smoking article.

28. The method of claim 25, wherein detecting the smoking action by the user comprises detecting, by the sensor circuit, a change in power of the battery element, wherein the sensor circuit is configured to capture the at least one use data characteristic of the smoking action only when the battery element of the electronic smoking article is active.

* * * * *